United States Patent [19]
Amundson et al.

[11] Patent Number: 5,484,449
[45] Date of Patent: Jan. 16, 1996

[54] TEMPORARY SUPPORT FOR A BODY LUMEN AND METHOD

[75] Inventors: Rodney R. Amundson, Lindstrom; Vincent W. Hull, Fridley; Robert S. Schwartz, Rochester; Rodney G. Wolff, Minnetonka Beach, all of Minn.

[73] Assignee: Medtronic, Inc., Minneapolis, Minn.

[21] Appl. No.: 167,279

[22] Filed: Dec. 13, 1993

Related U.S. Application Data

[63] Continuation-in-part of Ser. No. 818,649, Jan. 7, 1992, abandoned.

[51] Int. Cl.⁶ .................................................. A61M 25/10
[52] U.S. Cl. ........................... 606/108; 606/198; 606/194
[58] Field of Search ...................................... 606/108, 198, 606/191, 195, 194; 623/1, 12

[56] References Cited

U.S. PATENT DOCUMENTS

| | | |
|---|---|---|
| 4,512,338 | 4/1985 | Balko et al. ............................. 606/108 |
| 4,762,129 | 8/1988 | Bonzel ..................................... 604/96 X |
| 4,860,742 | 8/1989 | Park . |
| 4,878,906 | 11/1989 | Lindemann et al. ................. 606/108 X |
| 4,886,062 | 12/1989 | Wiktor . |
| 4,913,141 | 4/1990 | Hillstead . |
| 4,994,069 | 2/1991 | Ritchart . |
| 4,998,539 | 3/1991 | Delsanti . |
| 5,000,743 | 3/1991 | Patel . |
| 5,007,926 | 4/1991 | Derbyshire . |
| 5,017,407 | 5/1991 | Termin . |
| 5,019,085 | 5/1991 | Hillstead . |
| 5,019,090 | 5/1991 | Pinchuk . |
| 5,035,706 | 7/1991 | Gianturco . |
| 5,190,058 | 3/1993 | Jones . |
| 5,222,971 | 6/1993 | Willard . |

*Primary Examiner*—Michael H. Thaler
*Attorney, Agent, or Firm*—Daniel W. Latham; Harold R. Patton

[57] ABSTRACT

A stent and catheter device for temporary support of body lumens. The stent has a generally cylindrical continuous winding providing radial support from within a body lumen after implantation which can be implanted and removed by a balloon catheter. The stent is provided with an elongated lead attached to the proximal end of the winding and means at a proximal end of the lead and remote from the winding for uncoiling the winding to facilitate its removal in an opened condition with minimal tissue damage. This stent and catheter device is especially useful as a temporary supporting device for repairing damage to blood vessels caused during angioplasty procedures.

14 Claims, 4 Drawing Sheets

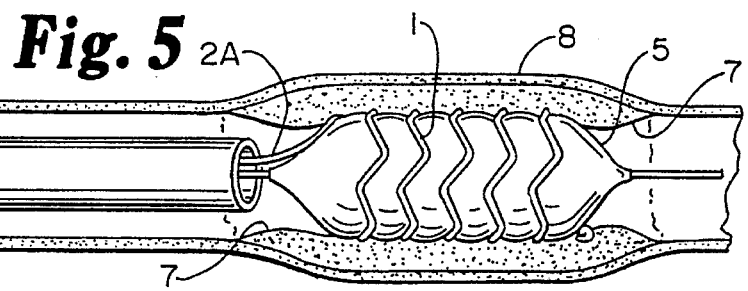
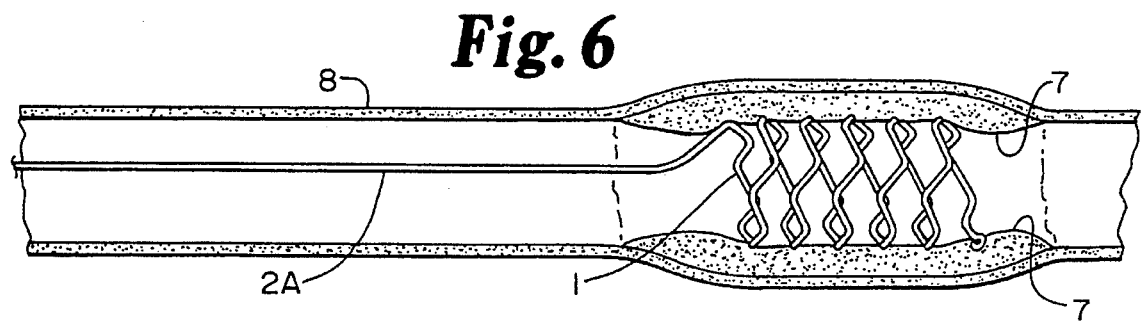
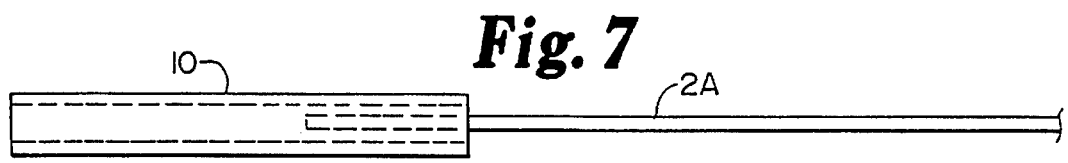
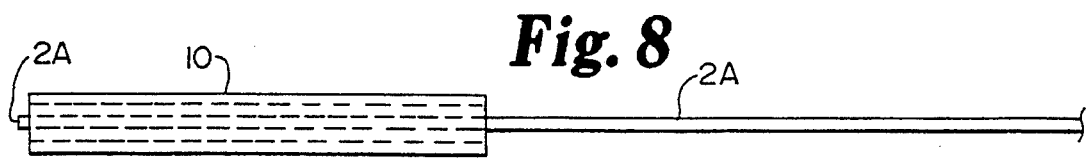
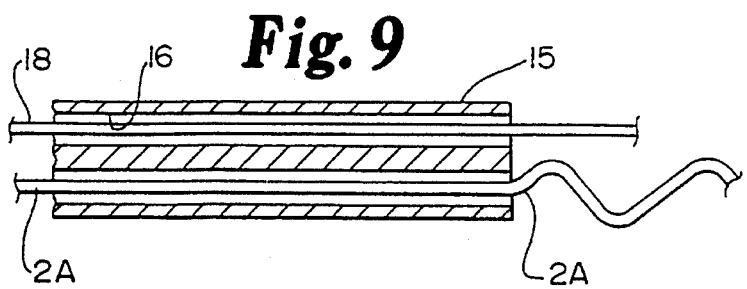

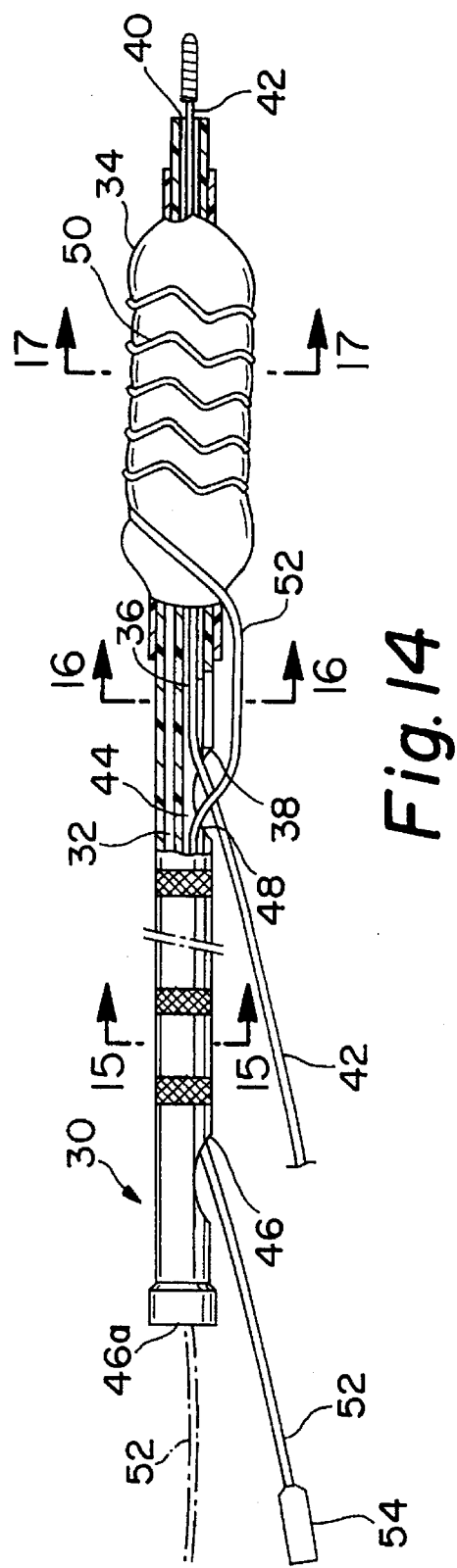
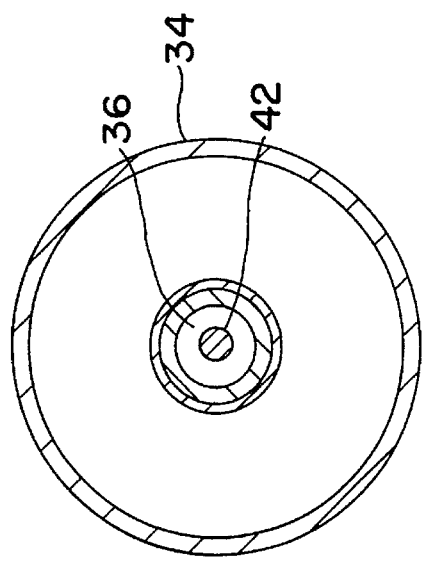
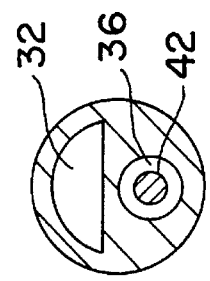
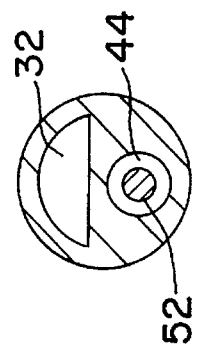

5,484,449

TEMPORARY SUPPORT FOR A BODY LUMEN AND METHOD

This is a continuation-in-part of U.S. Ser. No. 07/818,649 filed Jan. 7, 1992, now abandoned.

BACKGROUND OF THE INVENTION

This invention relates to intraluminal stent implants for maintaining patency of a body lumen in humans and animals and especially to such implants for use in blood vessels. The present invention comprises an improvement to stents which are generally cylindrical in shape and which are made up of a continuous winding such as that disclosed in U.S. Pat. No. 4,886,062 which is incorporated herein by reference. This type of stent is typically fitted over an inflatable element of a typical balloon catheter for implantation and is intended to act as a prosthesis stent which is implanted transluminally. This type of intravascular stent can be enlarged radially by inflation of the balloon after having been introduced percutaneously, transported transluminally and positioned at a desired location by means of the balloon catheter.

An important use of these stents is found in situations where part of the vessel wall or stenotic plaque blocks or occludes blood flow in the vessel. Dilation of the blood vessel is usually undertaken to correct a blood vessel occlusion i.e., a balloon catheter is utilized in a PTCA procedure to enlarge the occluded portion of the blood vessel. However, the dilation of the occlusion can form flaps, fissures and dissections which threaten re-closure of the dilated vessel. Implantation of a stent can provide support for such flaps and dissections and thereby prevent reclosure. However, such stents are not always easily removed or withdrawn.

In U.S. Pat. No. 5,019,090 issued to Pinchuk, a stent withdrawal procedure is disclosed in which a snare catheter is used to remove a stent. The snare catheter with a hook at its distal end is inserted into the blood vessel until the hook can snare a portion of the stent. The stent then uncoils as it is pulled from the blood vessel. However, this procedure cannot always be relied upon to withdraw the stent without injury to the blood vessel since it can be difficult to hook the expanded stent in a way that avoids damage to the blood vessel and also since the stent can easily become folded or crimped during the withdrawal procedure if the stent is hooked at an intermediate loop. It would therefore be desirable to provide a wire stent that can be applied to support flaps, fissures and dissections following angioplasty procedures and which also provides for simplified withdrawal when that support is no longer needed.

SUMMARY OF THE INVENTION

These and other objects have been accomplished by the stent of the present invention. We have discovered a device for providing temporary support to a body lumen which includes a balloon catheter, a continuous stent winding around the balloon, an elongated lead permanently attached to one of the ends of the stent and gripping means at the second end of the lead remote from the winding for grasping and withdrawing the lead, thereby uncoiling the winding and facilitating its removal in an opened condition. This invention can be particularly useful in coronary angioplasty procedures since it has been found that stent implantation need not be permanent in order to secure flaps and dissections in place following angioplasty procedures. The incorporation of a lead at a proximal end of the wire stent allows the stent to be delivered to the site of the occlusion by catheter and expanded conventionally. The stent, together with its permanently attached lead, then remains implanted for a period of time required to secure any flaps or dissections in place. The stent is then removed by pulling on the proximal end of the lead and uncoiling the expanded portion of the stent. Additional safety in the withdrawal procedure can also be afforded by the use of some means for centering the stent in the blood vessel as it is withdrawn. For example, a catheter or, most preferably, a multi-lumen catheter with a centering balloon can be used to center and straighten the stent as it is withdrawn.

The present invention also encompasses a rapid exchange type of catheter device for providing temporary support to a body lumen which includes a guidewire, a rapid exchange balloon catheter which has a guidewire lumen of the rapid exchange type extending from an opening near the proximal end of the balloon to an opening distal to the balloon which slideably receives the guidewire. A stent made from a continuous winding is on the balloon with an elongated lead attached to the wire of the winding. The balloon catheter also includes another lumen which extends from the proximal end of the catheter to an opening immediately adjacent to the balloon which accommodates the elongated lead and allows it to extend to the proximal end of the catheter. At its proximal end of the elongated lead, a handle, loop or some other gripping means is employed for grasping and withdrawing the lead. In operation, the guidewire is placed into the body lumen to be supported and the catheter is placed over the guidewire and into the body lumen with the balloon and stent winding positioned at the portion of the body lumen to be supported. The balloon is then inflated to radially expand the stent winding and is subsequently deflated to leave the stent winding in supporting contact with the body lumen. This support is maintained for a desired period of time which can be from a few minutes to hours (if necessary). Since blood flow is restored when the balloon is deflated, there is no need to remove the catheter from the body lumen during this period. The lead can then be withdrawn through the catheter lumen to effect the uncoiling of the winding and removal of the winding in an opened condition. This procedure allows the use of a rapid exchange catheter without the danger that the guidewire will become entangled with a separate lead extending from the stent.

BRIEF DESCRIPTION OF THE DRAWINGS

FIG. 5 is similar to FIG. 4 showing the balloon being inflated and the stent being radially expanded, illustrating an angioplasty procedure coupled with a simultaneous deployment and implantation of a prosthesis stent;

FIG. 6 is a view similar to FIG. 5 showing the prosthesis stent implanted and plaque compressed and retained after removal of the balloon.

FIGS. 7 and 8 show another embodiment of the invention;
FIG. 9 shows an extraction device and method according to the invention;

FIG. 14 is a cut-away elevational view of a rapid exchange catheter device according to the present invention.

FIGS. 15–17 are cross-sections through the device shown in FIG. 14.

DETAILED DESCRIPTION OF THE INVENTION

The stent of the present invention is a radially expandable stent for implantation within a body lumen having a continuous winding defining a generally cylindrical shape. A stent of this type is described, for example, in U.S. Pat. No. 4,886,062 issued to Wiktor which is incorporated herein by reference. The stent of the present invention also has an elongated lead permanently attached to the proximal end of the stent winding and extending away therefrom in a proximal direction and means at a proximal end of the lead remote from the winding for uncoiling the winding to facilitate its removal in an opened condition.

Figure 1:
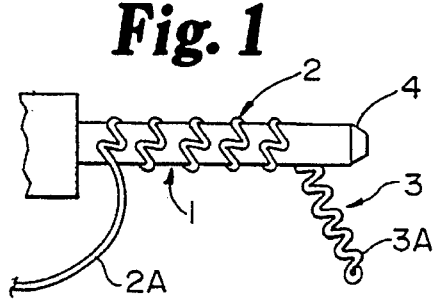
FIG. 1 is a side elevation of a preferred embodiment of a stent according to this invention being wound on a mandrel.

Therefore, the configuration to which this invention in particularly directed is shown in FIG. 1. A stent wire 2 (having a preferred diameter in the range of about 0.005 inch to 0.010 inch) is initially preformed into a two-dimensional zig-zag form 3, basically creating a flat expandable band 3A. The zig-zag pattern can vary as to its shape and the tightness of the reversing bends, but for reasons of simple description a typical sinusoidal form is chosen to depict the band's construction.

In order to create coiled stent 1, and to have it assume an initial configuration as shown at I in FIG. 1, and also the subsequently radially expanded condition as shown in FIG. 5, a length of preformed band 3A is wrapped or coiled on a suitable mandrel 4 in a manner similar to that of winding a simple helical spring. Again this is as shown in FIG. I and provides the coiled configuration 1. Care is taken to form the wire band 3A flat around the mandrel with little or no tension to prevent premature linear expansion of band 3A. The band 3A can be terminated at a distal end by a free end loop as shown or by securing the end loop to the last coil of the winding.

Figure 2:
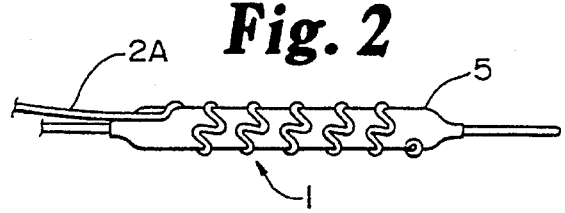
FIG. 2 is a side elevation showing an overall view of a stent prosthesis according to this invention fitted over a deflated balloon.

Once the zig-zag band 3A is wound into a coiled cylindrical shape 1, it is removed from the mandrel 4, and is placed over a suitable expandable diameter device such as an inflatable balloon 5 typically used for angioplasty procedures. This is shown in FIG. 2. A suitable crimping tool (not shown) may be used to tighten the stent over the balloon. Manual operation of squeezing the stent over the balloon is also acceptable.

Controlled radial expansion of the stent is accomplished by the force generated in inflating the balloon. When acted upon by the inflating balloon the stent, being characterized by the zig-zag preformed wire band 3A, is subsequently formed into an open-ended cylindrical shape. By design and intent it is capable of expanding radially.

The radial expansion in effect is achieved by controlled deformation and tension applied to the sinusoidal pattern of the preformed wire band 3A. The low memory metal used for the fabrication of the wire formed stent assures that the radially expanded stent stays expanded thus fulfilling its primary intent and function to provide support in a body lumen such as a blood vessel for any flaps or dissections in the lumen wall.

For purposes of better understanding this invention detailed reference is made to FIGS. 1–6. The preferred embodiment of this invention is shown and described in an application for angioplasty; however, it is understood that other applications not specifically mentioned herein are possible and no limitations in scope of this invention are intended or implied.

As seen in FIG. 1, a length 2A of wire 2 extends off a mandrel 4 and is not wound thereon nor is it formed in the zig-zag bend or shape as previously described. This length 2A functions as an elongated, permanently attached lead for the stent and may be of various lengths. It may extend the entire length of a catheter in which case a length of four or five feet may be used or even longer lengths where certain catheter exchange procedures are to be used. It may also be only a few inches long in order to provide a ready connection to another element which can effect the uncoiling of the stent winding. Lead 2A may be an integral extension of the proximal end of continuous wire 2 or it may be otherwise permanently attached to the proximal end of the wire as shown in the Figures by brazing, welding, adhesives, crimping, heat shrinking etc. Preferably the stent and lead are fabricated from a single piece of wire as shown with the stent formed integrally on the distal end thereof, the remaining length of wire functioning as the lead portion on the other end. Alternatively, the lead may be fabricated from polymeric tubing which may be secured to the stent wire by heat-shrinking the tubing.

The wire used for the stent winding and elongated lead may be made of drawn low-memory level material such as tantalum, stainless steel, titanium ASTM F63-83 Grade I or high carat gold K 19–22. Copper alloy typically 110 when properly coated with polyester or Teflon can also be used. Titanium and gold are biologically compatible and inert and require no special treatment. Tantalum is the preferred stent material.

In FIG. 2 it is seen that stent 1 is centrally located and positioned with respect to the length of balloon 5 and that flat preformed wire band 3A turns are evenly spaced so that when stent 1 is expanded as shown in FIG. 5 and FIG. 6, stent 1 will provide even support inside vessel 8 and be able to resist external loading. Elongated lead 2A is merely left to extend proximally from the end of the stent.

Figure 3:
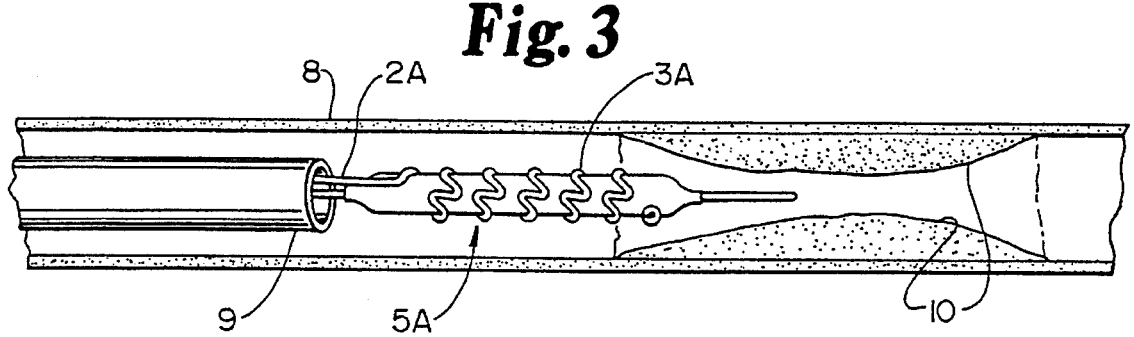
FIG. 3 shows the balloon and stent assembly of FIG. 2 advanced within a vessel, approaching a partial occlusion.
Figure 4:
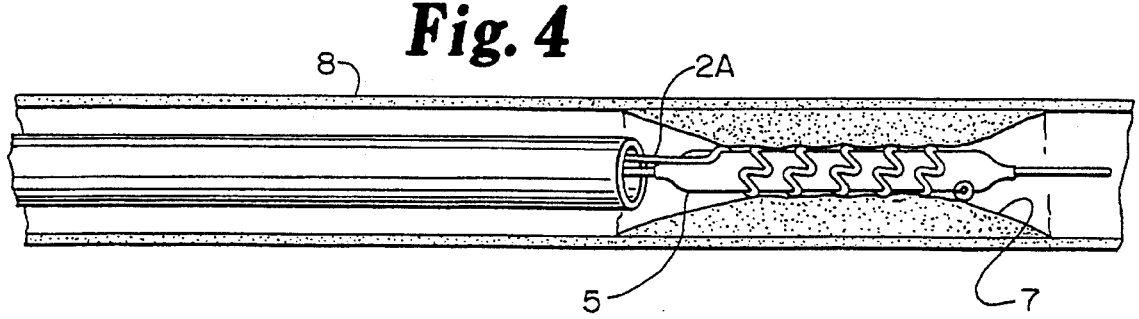
FIG. 4 is similar to FIG. 3 showing the balloon and stent assembly inside a partially occluded vessel.

In FIG. 3 it is seen how balloon and stent assembly 5A emanate from guiding catheter 9 inside vessel 8 and are advanced towards partial occlusion 10. It will be appreciated by those skilled in the art that although the balloon and stent assembly 5A is shown with an undilated occlusion 10, the stent of the present invention can also be used in pre-dilated vessels in order to support flaps or dissections caused by the dilation procedure. It will also be appreciated that a conventional guidewire may be employed to assist deployment of the assembly 5A into the occlusion 10. In FIG. 4 it is seen how balloon and stent assembly 5A are located in occlusion 10 within artery 8, balloon 5 still being deflated. Once positively placed, such as within occlusion 10, balloon 5 is inflated using standard angioplasty procedures and techniques. As balloon 5 expands, so does stent 1 as shown in FIG. 5. The expanding balloon 5 together with stent 1 contacts the plaque 7 and expands the vessel 8. With the angioplasty procedure completed, balloon 5 is deflated and withdrawn leaving stent 1 firmly implanted within vessel 8. Previously occluded vessel 8 is now supported by stent 1 and patency is restored. Again, elongated lead 2A is merely left in place, extending in a proximal direction from the end of the stent.

FIG. 6 shows stent 1 firmly implanted and imbedded in plaque 7 providing both adequate support as well as a vessel 8 without protrusions, flaps and dissections to obstruct blood flow. The stent 1 may then remain in place for the period of time required for any flaps or dissections caused by the dilation of the balloon 5 to re-adhere to the wall of the vessel 8. Since the angioplasty balloon is deflated during this period, blood flow through the lumen is not constricted even though the balloon catheter remains positioned in the body lumen at the site of the angioplasty. When removal is desired, grasping the proximal end of elongated lead wire 2A and gently pulling on it results in the uncoiling of the stent. The lead is continually pulled until it is completely removed from the guiding catheter 9. The result is removal of a long piece of relatively straight wire. If desired, the stent can be pulled out at the same time as the balloon angioplasty catheter, before the balloon angioplasty catheter is removed or after the balloon angioplasty catheter is removed. The stent can also be removed at the same time as the removal of the guiding catheter or before or after removal of the guiding catheter although most physicians would find it preferable to leave the guiding catheter in place until the stent is removed.

This improvement in the stent design greatly accommodates retrievability. The sinusoid waves or zig zag form in the stent wire straighten during the retrieval procedure and the procedure is completed with minimal trauma to the vessel wall.

In a preferred embodiment it has been found desirable to provide a means for stiffening the lead and to provide gripping means by increasing the size of the lead at its proximal end or by providing some other form of handle in order to make it easier for the physician to handle the lead and withdraw the stent; for example, by enclosing the proximal end of the elongated lead in a metal tube or the like as shown in FIG. 7 or FIG. 8. In these FIGS. the elongated lead 2A is inserted in a stainless steel tube 10. The tube may be only a few inches long or it may extend for substantially the entire length of the lead. A tube with an OD of 0.012–0.018 inches could be used, for example. It may be inserted partially as shown in FIG. 7 or completely as shown in FIG. 8. The end 2A and tube are then permanently united a by soldering, brazing, epoxying or the like.

Figure 10:
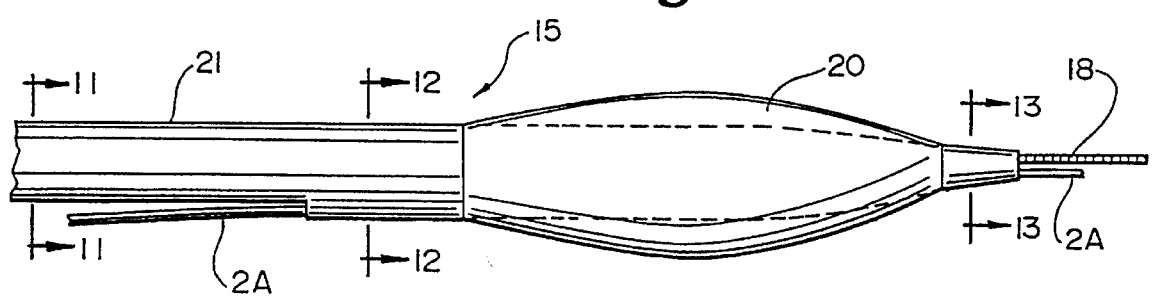
FIG. 10 shows an extraction device with centering balloon.
Figure 11:
FIGS. 11–13 are cross-sections through the device shown in FIG. 10.
Figure 12:
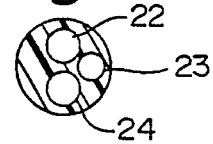
Figure 13:
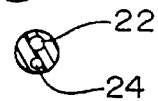

In a preferred embodiment, the invention also includes a catheter device for removing a stent having a continuous winding from a body lumen. The device comprises a catheter with a lumen at a distal end of the catheter which is designed to receive an elongated lead attached to a proximal end of the stent winding. The lead then extends to a proximal end of the catheter where it provides means for uncoiling the stent winding to facilitate its removal in an opened condition. The lead is preferably stiffened to allow the catheter to be guided over the lead without bending or crimping the lead. The use of such a device for removal of the stent may be enhanced by providing means for centering and straightening the stent as it is withdrawn. For example, as shown in FIG. 9 by the use of a stent removal device 15 including a multi-lumen catheter with or without a centering balloon. Use of the centering balloon is preferred. With such a device, one lumen 16 may be used for a guide wire 18 to facilitate insertion of the device to the implantation site. If a centering balloon is included with the device, it is inflated to position the device and it steadies the device. The elongated lead 2A is received in the other lumen and is pulled therethrough for extraction. As this occurs, the zig zag form of stent wire uncoils and contacts the distal edge of the catheter tube and straightening thereof is greatly facilitated through such contact without risk of trauma to the vessel walls. The use of a centering balloon facilitates the withdrawal of the elongated lead 2A by drawing the lead to the center of the vessel wall as shown in FIG. 10.

A preferred device 15 with a centering balloon 20 attached to a guiding catheter 21 is shown in FIG. 10 and FIGS. 11–13. A guidance lumen 22 runs through the entire catheter structure. A balloon inflation lumen 23 extends only to the balloon. The stent wire lumen 24 only runs through the distal end portions of the catheter device structure.

FIGS. 14–17 show a rapid exchange device for providing temporary support to a body lumen according to the present invention. The device depicted includes a rapid exchange catheter 30 which has an inflation lumen 32 extending from the proximal end of the catheter 30 to the distal end of the catheter 30 and in communication with the balloon 34. The balloon 34 is shown in an inflated condition. A guidewire lumen 36 extends from an opening 38 immediately proximal to the balloon 34 to an opening 40 distal to the balloon 34. A guidewire 42 is slideably received in the guidewire lumen 36. A second lumen 44 extends from an opening 46 (or optionally at opening 46A) at the proximal end of the catheter 30 to an opening 48 immediately adjacent to the balloon 34. A continuous stent winding 50 is disposed around the balloon 34 in a generally cylindrical shape. A conventional inflation device (not shown) can be used for inflating the balloon 34 to radially expand the winding 50 into supporting contact with the body lumen. An elongated lead 52 is attached at a first end to one of the end wires of the winding 50 and slideably extends through the second lumen 44 of the catheter 30 to the proximal end of the catheter 30. As shown, the lead 52 can be an integral extension of the winding 50. At the distal end of the catheter 30, the lead 52 passes through the opening 48 of lumen 44. This opening 48 could conceivably be placed at any point near the distal end of the catheter 30. As shown, the position of the opening 48 for the lead 52 with respect to opening 38 for the guidewire 42 has the advantage that a two lumen tubing can be used for the body of the catheter 30 since one lumen of the tubing can supply lumens for both the guidewire 42 and lead 52. In other configurations a tubing with a third lumen may be needed. When the openings 38, 48 are close together, they would preferably be created to direct the guidewire 42 and lead 52 away from each other to the extent possible in order to prevent friction or entanglement between them. At the proximal end of the catheter 30, the lead 52 can emerge from the lumen 44 at opening 46 or optionally at opening 46a. An enlarged portion 54 supplies gripping means at the end of the lead 52 for grasping and withdrawing the lead 52. The gripping means can also comprise stiffening structures such as a metal tube at the proximal end of the lead 52 or other conventional expedients to improve a person's grip on a fine wire or the like. Where the continuous winding 50 has a zig-zag configuration (as shown), the opening 48 at the distal end of the catheter is able to straighten the zig-zags sufficiently as the winding is pulled into the opening to bring the winding 50 out through the lumen 44.

In operation, this embodiment is able to temporarily support a body lumen. First, the guidewire is placed into the body lumen and positioned such that it traverses the portion of the body lumen to be supported. The rapid exchange catheter is then placed over the guidewire and into the body lumen with the balloon and continuous winding positioned at the portion of the body lumen to be supported. The balloon is then inflated to radially expand the continuous winding into supporting contact with the body lumen and then deflated to leave the radially expanded continuous winding in supporting contact with the body lumen. Support of the body vessel is then maintained with the radially expanded continuous winding for the period of time believed to be required to support any flaps, fissures or dissections in the lumen wall. The lead is then withdrawn through the catheter lumen by pulling the lead at the proximal end of the lead thereby causing the uncoiling of the winding and removal of the winding in an opened condition. In some instances, the winding may have a tendency to tighten around the balloon catheter as it is withdrawn if the catheter is still positioned within the winding when the lead is pulled back. This can be easily avoided by withdrawing the balloon catheter slightly to place the distal end of the balloon catheter at the proximal end of the winding before attempting to withdraw the lead. Alternatively, if it is found that a few coils of the winding have tightened around the catheter so that the winding cannot be completely withdrawn, the catheter and the retained winding can still be withdrawn as a unit without hazard to the patient.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for providing temporary support to a body lumen comprising:
   (a) a catheter having a proximal end and a distal end and a balloon at the distal end:
   (b) a continuous winding on the balloon, the winding comprising a wire having a first end and a second end, the wire wound into a generally cylindrical shape around the balloon;
   (c) inflation means for inflating the balloon to radially expand the winding into supporting contact with the body lumen:
   (d) an elongated lead having a first end and a second end, the first end attached to one of the first and second ends of the wire of the winding: and
   (e) gripping means at the second end of the lead remote from the winding for grasping and withdrawing the lead, thereby uncoiling the winding and facilitating its removal in an opened condition, wherein the lead at least partially occupies a lumen at the distal end of the catheter.

2. The device of claim 1 wherein the lead occupies the lumen from a point near the distal end of the catheter to the proximal end of the catheter.

3. A device for providing temporary support to a body lumen comprising:
   (a) a guidewire;
   (b) a rapid exchange catheter having a proximal end and a distal end and a balloon at the distal end, the catheter having a first lumen at a distal end of the catheter extending from an opening immediately proximal to the balloon to an opening distal to the balloon which slideably receives the guidewire and a second lumen extending from the proximal end of the catheter to an opening immediately adjacent to the balloon;
   (c) a continuous winding on the balloon, the winding comprising a wire having a first end and a second end which is wound into a generally cylindrical shape around the balloon;
   (d) inflation means for inflating the balloon to radially expand the winding into supporting contact with the body lumen;
   (e) an elongated lead having a first end and a second end, the first end attached to one of the ends of the wire of the winding and extending through the second lumen of the catheter to the proximal end of the catheter; and
   (f) gripping means at the second end of the lead remote from the winding for grasping and withdrawing the lead, thereby uncoiling the winding and facilitating its removal in an opened condition.

4. The device of claim 3 wherein the lead portion is an integral extension of the winding.

5. The device of claim 3 wherein the lead is a wire.

6. The device of claim 3 wherein the lead is a tube.

7. The device of claim 6 wherein the tube is shrink tubing.

8. The device of claim 3 wherein the gripping means comprises stiffening means at the proximal end of the lead.

9. The device of claim 8 in which the stiffening means comprises a metal tube into which the lead is inserted.

10. The device of claim 3 wherein the gripping means comprises a larger lead diameter near the second end than near the first end.

11. The device of claim 3 wherein the continuous winding has a zig-zag configuration and the device includes means at the distal end thereof for straightening the zig-zags as the winding is removed.

12. A method for temporarily supporting a body lumen comprising:
   (a) providing a guidewire;
   (b) providing a rapid exchange balloon catheter having a proximal end and a distal end and a balloon at the distal end, the catheter having a guidewire lumen which slideably receives the guidewire and a second lumen extending from the proximal end of the catheter to an opening immediately adjacent to the balloon;
   (c) providing a continuous winding on the balloon of the balloon catheter, the winding wound into a generally cylindrical shape around the balloon with an elongated lead attached to the winding and extending through the second lumen of the catheter;
   (d) placing the guidewire into the body lumen to be supported;
   (e) placing the catheter over the guidewire and into the body lumen with the balloon and continuous winding positioned at the portion of the body lumen to be supported;
   (f) inflating the positioned balloon to radially expand the continuous winding into supporting contact with the body lumen;
   (g) deflating the inflated balloon, thereby leaving the radially expanded continuous winding in supporting contact with the body lumen;
   (h) maintaining the support of the body vessel with the radially expanded continuous winding for a desired period of time; and
   (i) withdrawing the lead after the desired period of time through the catheter lumen at a point remote from the winding to effect the uncoiling of the winding and removal of the winding in an opened condition.

13. The method of claim 12 wherein the winding has a zig-zag configuration and the step for withdrawing the lead also includes straightening the zig-zags as the winding is removed.

14. The method of claim 12 wherein immediately prior to the step of withdrawing the lead the balloon catheter is withdrawn to place the distal end of the balloon catheter at the proximal end of the winding.

* * * * *